(12) United States Patent
Smith et al.

(10) Patent No.: US 9,597,457 B2
(45) Date of Patent: Mar. 21, 2017

(54) PISTON ROD FOR A DRUG DELIVERY DEVICE AND DRUG DELIVERY DEVICE COMPRISING A PISTON ROD

(71) Applicant: SANOFI-AVENTIS DEUTSCHLAND GMBH, Frankfurt am Main (DE)

(72) Inventors: Christopher James Smith, Cheshire (GB); Stephen David Butler, South Staffordshire (GB); Mark Phillip Horlock, Cheshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 90 days.

(21) Appl. No.: 14/401,945

(22) PCT Filed: May 28, 2013

(86) PCT No.: PCT/EP2013/060913
§ 371 (c)(1),
(2) Date: Nov. 18, 2014

(87) PCT Pub. No.: WO2013/178601
PCT Pub. Date: Dec. 5, 2013

(65) Prior Publication Data
US 2015/0133872 A1    May 14, 2015

(30) Foreign Application Priority Data

May 30, 2012   (EP) ..................... 12170072

(51) Int. Cl.
*A61M 5/00*   (2006.01)
*A61M 5/315*   (2006.01)
*A61M 5/20*   (2006.01)

(52) U.S. Cl.
CPC ........... *A61M 5/31511* (2013.01); *A61M 5/20* (2013.01); *A61M 5/31515* (2013.01); *A61M 5/31543* (2013.01); *A61M 2205/19* (2013.01)

(58) Field of Classification Search
CPC .......... A61M 5/31511; A61M 5/31515; A61M 5/31543
See application file for complete search history.

(56) References Cited

U.S. PATENT DOCUMENTS 6,972,007 B2 *  12/2005  Geiser ................... A61M 5/24
                                                        604/135
2013/0079716 A1 *  3/2013  Thorley ............ A61M 5/31511
                                                        604/110

FOREIGN PATENT DOCUMENTS

CN          1780651 A      5/2006
CN        102076372 A      5/2011
(Continued)

OTHER PUBLICATIONS

International Search Report and Written Opinion for Int. App. No. PCT/EP2013/060913, mailed Jul. 2, 2013.
(Continued)

*Primary Examiner* — Deanna K Hall
(74) *Attorney, Agent, or Firm* — McDonnell Boehnen Hulbert & Berghoff LLP

(57) ABSTRACT

A piston rod for a drug delivery device comprises a main body and an engagement means for engaging the piston rod with a part of the drug delivery device. The engagement means are retractable relatively the main body for enabling a disengagement of the engagement means from the part of the drug delivery device.

12 Claims, 4 Drawing Sheets

(56) References Cited

FOREIGN PATENT DOCUMENTS

| | | |
|---|---|---|
| WO | 02/07812 | 1/2002 |
| WO | 2004/078226 A2 | 9/2004 |
| WO | 2009/132777 | 11/2009 |
| WO | 2011/075760 | 6/2011 |

OTHER PUBLICATIONS

Chinese Office Action for CN Application No. 201380026600.9, dated Jul. 18, 2016.

* cited by examiner

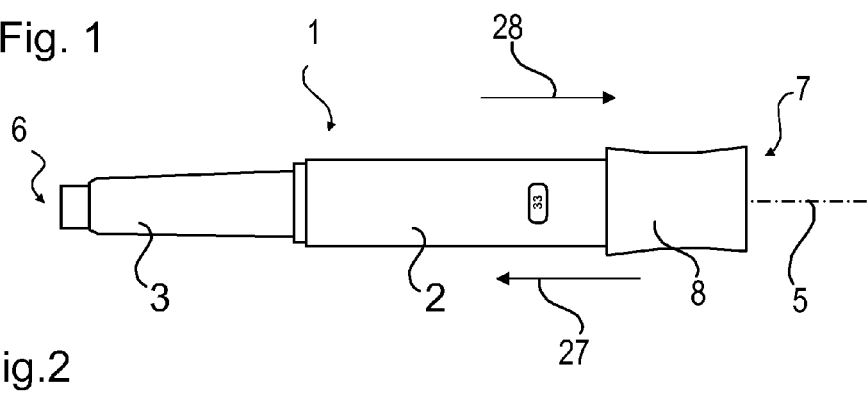
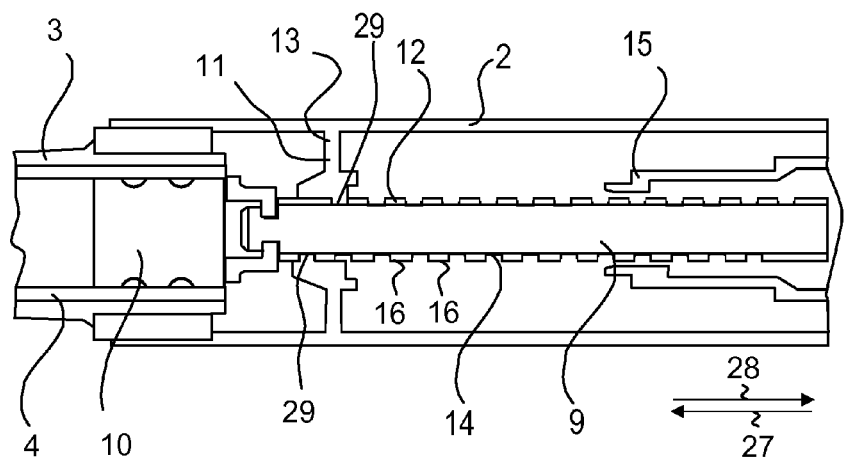
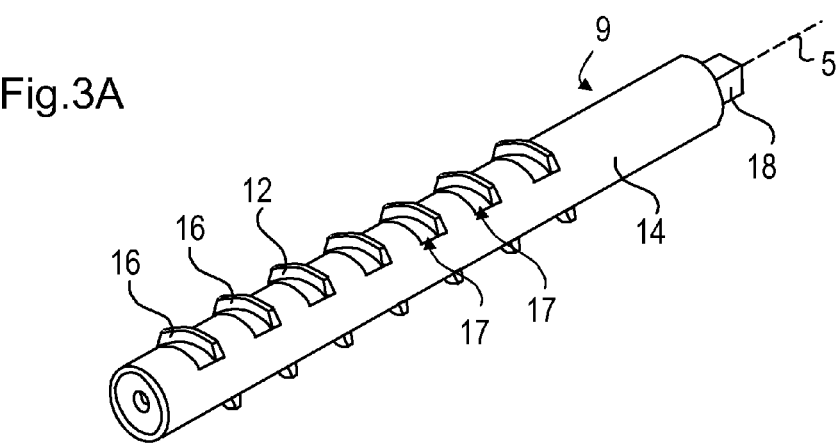

PISTON ROD FOR A DRUG DELIVERY DEVICE AND DRUG DELIVERY DEVICE COMPRISING A PISTON ROD

CROSS REFERENCE TO RELATED APPLICATIONS

The present application is a U.S. National Phase Application pursuant to 35 U.S.C. §371 of International Application No. PCT/EP2013/060913 filed May 28, 2013, which claims priority to European Patent Application No. 12170072.8 filed May 30, 2012. The entire disclosure contents of these applications are herewith incorporated by reference into the present application.

TECHNICAL FIELD

The present invention relates to a piston rod for a drug delivery device and to a drug delivery device comprising a piston rod. In particular, the piston rod and the drug delivery device may be configured such that the piston rod is resettable to a start position, thereby enabling an exchange of a medicament container and a re-usage of the drug delivery device.

BACKGROUND

The international patent application WO 2009/132777 A1 discloses a reusable medication delivery device.

SUMMARY

It is an object of the present invention to provide a piston rod and a drug delivery device providing an improved reset function.

According to a first aspect, a piston rod for a drug delivery device is disclosed. The piston rod comprises a main body and engagement means for engaging the piston rod with a part of the drug delivery device.

The term "piston rod" may be used for a component of a drug delivery device which, by carrying out a movement towards the dispensing end of the drug delivery device, causes medicament to be dispensed from the device. In particular, the piston rod may be configured to act on a bung or a piston in a medicament container, for example a cartridge, thereby causing medicament to be dispensed from the container. The piston rod may be configured for carrying out a combined axial and rotational movement during a dose dispense operation of a drug delivery device. As an example, the piston rod may have the shape of a simple rod or a lead-screw. The main body of the piston rod may comprise a longitudinal axis. The main body may have the shape of a rod, in particular a hollow rod.

The engagement means may, for example, comprise at least one thread form.

The thread form may be engageable with a thread form of a part of the drug delivery device. In particular, the thread form of the piston rod may be engageable with a nut member of the drug delivery device. In particular, the piston rod may be threadedly engageable with the nut member and may be configured to wind through the nut member in a distal direction during a dose dispense operation. As a further example, the engagement means may comprise teeth engageable with mating parts of the drug delivery device. As a further example, the engagement means may comprise other shapes of protrusions.

Preferably, the engagement means are retractable relatively to the main body of the piston rod for enabling a disengagement of the engagement means from the part of the drug delivery device.

A retraction of the engagement means relatively to the main body may mean that the engagement means are moved towards the main body such that they protrude from the main body at least to a minor extent than in a state where the engagement means are extended. As an example, the engagement means may be fully retracted into the main body such that they do not protrude from an outer surface of the main body. As a further example, the engagement means may be flush with an outer surface of the main body. As a further example, when refracted, the engagement means may still protrude from an outer surface of the main body, but to a minor extent. In all cases, preferably, by the retraction of the engagement means towards the main body, a disengagement of the engagement means from the part of the drug delivery device is enabled.

Accordingly, the piston rod may comprise two states, wherein in a first state, the engagement means are enabled to engage with a part of a drug delivery device and wherein in a second state, the engagement means are enabled to be disengaged from the part of the drug delivery device. The first state may be denoted as "operational state". Preferably, in a drug delivery device, the piston rod is in its operational state at least during a dose dispense operation. The second state may be denoted as "reset state". Preferably, in a drug delivery device, the piston rod is in its reset state during a reset operation.

Preferably, the main body comprises a longitudinal axis and the engagement means are radially retractable relatively to the longitudinal axis.

In this case, advantageously, a retraction of the engagement means may be carried out such that other parts of the drug delivery device are not affected or disturbed by a retraction of the engagement means.

In a preferred embodiment, the main body may comprise at least one opening through which the engagement means are retractable.

Preferably, the main body comprises a plurality of openings through which the engagement means are retractable. As an example, the engagement means may have the shape of thread forms, wherein each thread form extends through an opening and is retractable through the opening.

By a piston rod comprising retractable engagement means a reset operation of a drug delivery device may be facilitated. In particular, when a cartridge is exchanged, the piston rod may have to be moved back towards a start position such that the drug delivery device can be used with a new cartridge. For example, the piston rod may be pushed back or wound back in the proximal direction. The start position may be the most proximal position of the piston rod relatively to a housing of the drug delivery device.

In this context, the term "proximal end" of the drug delivery device, or a component thereof, may refer to that end of the device or the component which is furthest away from a dispensing end of the device. The term "distal end" of the drug delivery device or a component thereof may refer to that end of the device or the component which is closest to the dispensing end of the device.

The disengagement of the piston rod from a part of the drug delivery device, for example from a nut member of the drug delivery device, may facilitate a reset operation of the piston rod. In particular, a movement of the piston rod to its start position may be unhindered by an engagement with the part of the drug delivery device. In one embodiment, when the piston rod is disengaged, a reset operation may require a reduced force. In a further embodiment, a reset operation may only be possible when the piston rod is disengaged.

In a preferred embodiment, the piston rod comprises a switching member configured such that an operation of the switching member causes at least one of an extension or retraction of the engagement means relative to the main body.

In particular, by an operation of the switching member, the engagement means may be pulled towards the main body for causing a retraction of the engagement means or may be pushed out of the main body for causing an extension of the engagement means.

The switching member may be at least partially located inside the main body of the piston rod.

In particular, the switching member may extend along a central part of the main body. Preferably, the switching member may extend along a longitudinal axis of the main body.

In an embodiment, the switching member may protrude out from the main body.

In particular, the switching member may protrude out of a proximal end of the main body. Thereby, a part of the switching member may be accessible from the outside of the main body. For an operation of the switching member, the part protruding out of the main body may be operated.

In one embodiment, the switching member is configured such that an operation of the switching member comprises a rotational movement of the switching member.

In particular, the piston rod may be configured such that in one rotational orientation of the switching member relative to the main body, the piston rod is in its operational state and in a different rotational orientation of the switching member the piston rod is in its reset state. Preferably, by rotating the switching member, a switching of the piston rod from its operational state to its reset state or vice versa may be effected. For example, the switching member may be rotated by an angle of 180° for switching the piston rod from its operational state to its reset state.

In a further embodiment, the piston rod may be configured such that an operation of the switching member comprises a translational movement of the switching member relative to the main body.

As an example, when the switching member is moved from a first axial position relative to the main body to a second axial position relative to the main body, the piston rod may be switched from its operational state to its reset state or vice versa.

The switching member may comprise at least one protrusion.

The piston rod may be configured such that the engagement means is at least one of being extended and retracted by an interaction of the engagement means with the protrusion.

In this context "interaction" may comprise a direct mechanical contact between the engagement means and the protrusion or an indirect mechanical contact, for example via a transmission element. In particular, the piston rod may be configured such that the engagement means are pushed out of the main body when the protrusion is located directly beneath the engagement means. When the protrusion is moved away from the engagement means, for example rotated or translated, the engagement means may be retracted relatively to the main body. In particular, the switching member may comprise a cam shaft.

The switching member may comprise a plurality of protrusions. The protrusions may protrude in different radial directions relative to a longitudinal axis of the main body. The protrusions may be located at a regular pitch. The piston rod may be configured such that a translational movement of the switching member by half the distance of the pitch causes the engagement means to change from their extended state to their retracted state or vice versa.

According to a further aspect, a drug delivery device comprising a piston rod is disclosed. The piston rod of the drug delivery device may have any structural or functional features of the piston rod as described above or below.

As an example, the drug delivery device may be an injection device, in particular a pen-type injection device. Preferably, the drug delivery device is a reusable device such that a drug receptacle can be exchanged and the device can be reused with a new drug receptacle.

In a preferred embodiment, the drug delivery device comprises a main housing and a cartridge holder attachable to and detachable from the main housing.

Preferably, the piston rod is resettable to a start position when the cartridge holder is detached from the main housing.

In particular, the engagement means of the piston rod may be retractable when the cartridge holder is detached from the main housing. Thereby, a reset operation of the piston rod to a start position may be facilitated.

In one embodiment, the drug delivery device may be configured such that a detachment of the cartridge holder causes a retraction of the engagement means. Preferably, the drug delivery device is configured such that an attachment of the cartridge holder causes an extension of the engagement means.

In particular, the piston rod may comprise a switching member as described above. The cartridge holder may be coupled to the switching member such that the switching member is operated by at least one of a detachment or attachment operation of the cartridge holder.

By a coupling of the engagement means to the cartridge holder, the engagement means may be automatically retracted by a detachment of the cartridge holder. Accordingly, a switching of the piston rod to its reset state may be automatically caused by a detachment of the cartridge holder. Furthermore, the engagement means may be automatically extended by an attachment of the cartridge holder. Accordingly a switching of the piston rod to its operational state may be automatically caused by an attachment of the cartridge holder.

In the case of an automatic retraction of the engagement means and/or an automatic extension of the engagement means only few steps may be required in order to exchange a cartridge of the device. In particular, after detaching a cartridge holder from the housing in order to replace the cartridge of the device, a user may simply need to move back the piston rod and re-attach the cartridge holder containing the new cartridge, without having to take any additional action regarding the disengagement of the piston rod from a part of the drug delivery device. By re-attaching the cartridge holder to the housing of the device, the part of the drug delivery device may automatically engage with the piston rod, again without requiring any additional actions of the user of the device.

In a further embodiment, the drug delivery device may comprise a dose member for setting and/or dispensing a dose of a medication. The drug delivery device may be configured such that a retraction of the engagement means may be caused by an operation of the dose member. Furthermore, the drug delivery device may be configured such that additionally or alternatively an extension of the engagement means may be caused by an operation of the dose member.

In particular, the piston rod may comprise a switching member as described above. The dose member may be coupled to the switching member such that the switching member is operated by an operation of the dose member.

The term "medicament", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2]

H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Further features, refinements and expediencies become apparent from the following description of the exemplary embodiments in connection with the figures.

FIG. 1 schematically shows a side view of a drug delivery device.

FIG. 2 schematically shows a sectional side view of a part of the drug delivery device of FIG. 1.

FIG. 3A shows a perspective view of a first embodiment of a piston rod in an operational state.

DETAILED DESCRIPTION

Figure 3B:
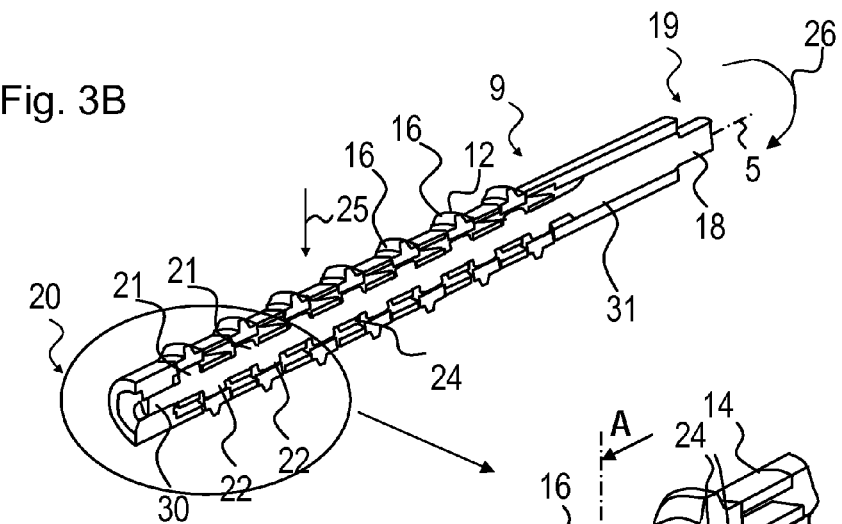
FIG. 3B shows a perspective sectional view of the piston rod of FIG. 3A.

Like elements, elements of the same kind and identically acting elements may be provided with the same reference numerals in the figures.

FIG. 1 shows a perspective side view of a drug delivery device 1. The device 1 extends along a longitudinal axis 5. The device 1 comprises a main housing 2 and a cartridge holder 3 attached to the main housing. The cartridge holder 3 houses a cartridge comprising a medicament. Preferably, the medicament is a liquid medicament, for example insulin. Preferably, the drug delivery device 1 is a reusable device such that the cartridge can be exchanged. For this aim, the cartridge holder 3 may be detached from the main housing 2, an empty cartridge may be replaced by a full cartridge and the cartridge holder 3 may be re-attached to the main housing 2.

The drug delivery device 1 comprises a dose member 8 for setting and dispensing a dose of a medication. In this context, the term "setting a dose" or "dose setting operation" may mean that the device 1 and, in particular, a drive mechanism of the device 1 is prepared for a subsequent dose dispense operation. In particular, the dose setting operation may be a step immediately preceding a dose dispense operation. As an example, the drug delivery device 1 may be a pull-push device such that the dose member 8 is pulled out of the housing 2 for setting a dose and is pushed towards the housing 2 for dispensing a dose. In a different embodiment, the device 1 may be a twist-push device such that for setting a dose, the dose member 8 is twisted and, thereby, may move helically outwards of the main housing 2. For dispensing the dose, the dose member 8 may be pushed towards the main housing 2.

The drug delivery device 1 comprises a distal end 6 and a proximal end 7. The term "distal end" of the drug delivery device 1 or a component thereof may refer to that end of the device or the component which is closest to the dispensing end of the device 1. The term "proximal end" of the drug delivery device 1 or a component thereof may refer to that end of the device or the component which is furthest away from the dispensing end of the device. The arrows 27 and 28 are used to indicate the distal resp. the proximal direction, i.e. the direction towards the distal end 6 resp. towards the proximal end 7.

The device 1 may be an injection device. A needle may be attached to the dispensing end of the device 1, i.e., at the distal end 6 of the device. In particular, the device 1 may be a pen-type injection device.

The device 1 may be a fixed dose device, i.e., the device may be configured such that the size of each dose is predetermined by the configuration of the device. In particular, a user is not enabled to vary the size of a dose. Alternatively, the device 1 may be a variable dose device, i.e., the device is configured such that the user is enabled vary the size of a dose.

FIG. 2 shows a sectional side view of a part of the drug delivery device of FIG. 1.

The drug delivery device 1 comprises a piston rod 9. The piston rod 9 is configured for transferring a force to a piston 10, thereby displacing the piston 10 in the distal direction 27 with respect to a cartridge 4. The piston 10 is retained within the cartridge 4. The piston 10 may seal the medication within the cartridge 4. The piston 10 expediently seals the interior of the cartridge 4 proximally. Movement of the piston 10 with respect to the cartridge 4 in the distal direction 27 causes medication to be dispensed from the cartridge 4 through its outlet during operation of the device 1.

The piston rod 9 comprises engagement means 12 for engaging the piston rod 9 with a part 11 of the device 1. In the shown embodiment, the part 11 of the device 1 is a nut member 13. The nut member 13 is fixed to the housing 2 such that relative movements between the nut member 13 and the housing 2 are prevented. Preferably, the nut member 13 is permanently fixed to the housing 2, in particular during dose set operations, dose dispense operations and during resetting operations of the device 1.

The nut member 13 guides the piston rod 9 in a dose dispense operation of the device 1. The engagement means 12 of the piston rod 9 comprise thread forms 16 protruding from a main body 14 of the piston rod 9. The thread forms 16 are configured to engage with thread forms 29 of the nut member 13. In a dose dispense operation, the piston rod 9 moves in the distal direction 27 and, thereby, winds through the nut member 13.

The movement of the piston rod 9 is caused by an operation of the dose member 8. In particular, the device 1 comprises a drive member 15 which transfers a force from the dose member 8 to the piston rod 9 and, thereby causes a movement of the piston rod 9. As an example, the drive member 15 may be coupled to the piston rod 9 such that a relative translational movement between the drive member 15 and the piston rod 9 is allowed and a relative rotational movement is prevented. Thereby, in a dose dispense operation, the drive member 15 may cause the piston rod 9 to rotate. Due to the threaded engagement of the piston rod 9 with the nut member 13, the piston rod 9 moves in the distal direction 27.

In FIG. 2, the piston rod 9 is in a start position, i.e., in its most proximal position relative to the main housing 2. Accordingly, no medicament has been dispensed from the cartridge 4 yet. In a dose dispense operation of the device 1 the piston rod 9 is displaced from its start position in the distal direction 27. I particular, the piston rod 9 incrementally winds itself out of the housing 2 in a distal direction 27 each time a dose of medicament is dispensed.

When the cartridge 4 is exchanged, the piston rod 9 may have to be moved back to its start position. Such a movement in the proximal direction 28 may be hampered by the engagement of the nut member 13 with the piston rod 9. In particular, when the piston rod 9 is engaged with the nut member 13, a movement of the piston rod 9 in a proximal direction 28 may not be possible at all or may require a large force. In order to facilitate a resetting of the piston rod 9 to a start position, the engagement means 12 may be configured to be retractable and, thereby, allow a disengagement from the nut member 13 during a reset operation.

FIG. 3A to 4B show a first embodiment of a piston rod 9 comprising retractable engagement means 12. The piston rod 9 may be used in a device 1 as shown in FIGS. 1 and 2 or in a different drug delivery device.

FIGS. 3A to 3D show the piston rod 9 in a state, wherein an engagement of engagement means 12 of the piston rod 9 with a part of a drug delivery device is enabled. This state may be denoted as "operational state" of the piston rod 9. In particular, the piston rod 9 may be in its operational state during a dose set and dose dispense operation of the device.

Figure 4A:
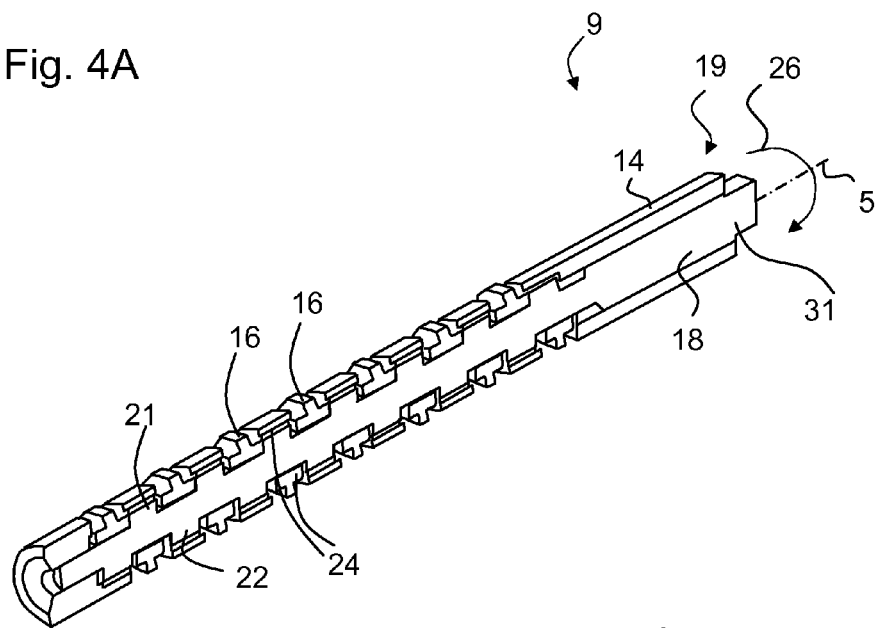
FIG. 4A shows a perspective sectional view of the first embodiment of the piston rod in a reset state.
Figure 4B:
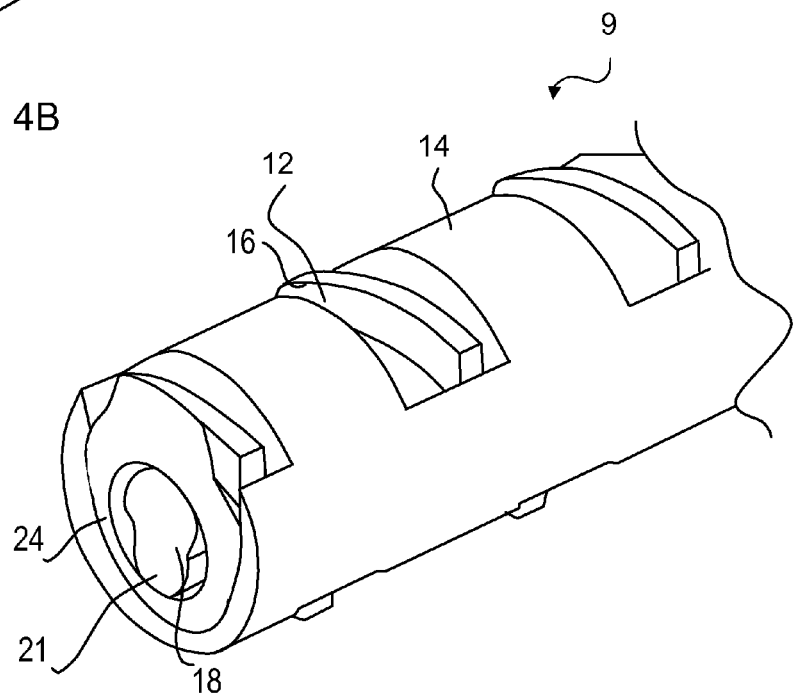
FIG. 4B shows a perspective cross-sectional view of the piston rod of FIG. 4A.

FIGS. 4A to 4B show the piston rod 9 in a state, wherein the engagement means 12 are retracted such that a disengament from the part of the drug delivery device is enabled. This stated may be denoted as "reset state" of the piston rod 9. In particular, due to the retraction of the engagement means 12, a resetting of the piston rod 9 towards its start position may be facilitated.

Now, turning to the operational state, FIG. 3A shows a perspective view of the piston rod 9. The piston rod 9 extends along a longitudinal axis 5, which may coincide with a longitudinal axis of a respective drug delivery device.

The engagement means 12 of the piston rod 9 comprise a plurality of thread forms 16. The thread forms 16 are configured for a threaded engagement with a part of a drug delivery device 1, for example a nut member 13 as shown in FIG. 2. The piston rod 9 is configured as a lead screw, wherein the screw thread formed by the thread forms 16 is interrupted in an axial direction.

The piston rod 9 comprises a main body 14. The main body 14 is shaped as a hollow rod comprising several openings 17 through which the thread forms 16 protrude.

The piston rod 9 comprises a switching member 18 configured to switch the piston rod 9 from an operational state as shown in FIGS. 3A to 3D to a reset state as shown in FIGS. 4A and 4B and vice versa. Preferably, the switching member 18 is also configured to hold the piston rod 9 in one of the states.

Figure 3C:
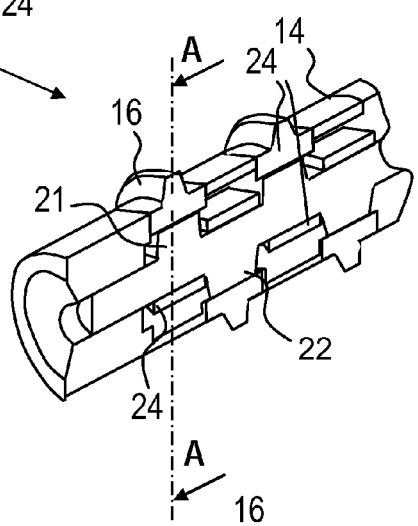
FIG. 3C shows an enlarged view of a part of the piston rod of FIG. 3B.
Figure 3D:
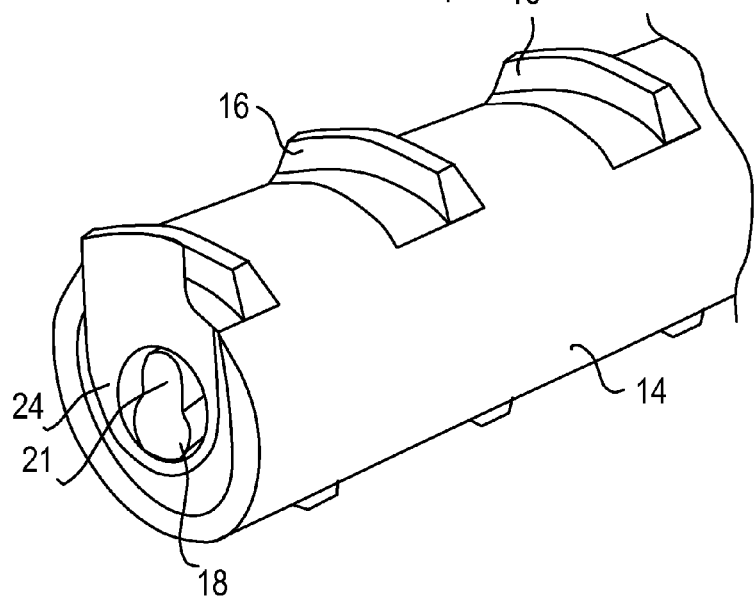
FIG. 3D shows a perspective cross-sectional view of the piston rod of FIG. 3C.

FIGS. 3B, 3C and 3D show sectional views of the piston rod 9 of FIG. 3A. In particular, FIG. 3B shows a perspective sectional view of the piston rod 9, wherein the section runs along the longitudinal axis 5 of the piston rod 9. FIG. 3C shows an enlarged view of a distal portion of the piston rod 9 of FIG. 3B. FIG. 3D shows a perspective cross-sectional view of the piston rod, wherein the cross-section runs along the line denoted by A-A in FIG. 3C.

As can be seen in FIGS. 3B, 3C and 3D, the switching member 18 is configured as an internal shaft running inside the main body 14 and extending along the longitudinal axis 5 of the piston rod 9. The switching member 18 comprises a distal end portion 30 and a proximal end portion 31, wherein both end portions 30, 31 are at least partially embedded in the main body 14 such that the switching member 18 is fixed in radial directions relative to the longitudinal axis 5. Preferably, at least one of the end portions 30, 31 comprises means for maintaining the switching member 18 and, thereby, the piston rod 9 in its current state. As an example, the end portions 30, 31 may comprise notches engaging with the main body 14 such that a certain force is required for overcoming the engagement and rotating the switching member 18.

The switching member 18 comprises a plurality of protrusions 21, 22, wherein the protrusions 21, 22 extend alternatingly in one radial direction of the switching member 18 and in an opposite radial direction of the switching member 18. The radial protrusions 21, 22 may function as cam lobes. Accordingly, the switching member 18 may function as a camshaft.

In particular, the radial protrusions 21, 22 are configured to push the engagement means 12 out of the main body 14 when the switching member 18 is in the orientation shown in FIGS. 3B, 3C and 3D. In particular, here, each radial protrusion 21, 22, is located directly beneath an opening 17 of the main body 14. This orientation of the switching member 18 may be denoted a "12 o'clock orientation". When the switching member 18 is rotated around the longitudinal axis 5 by an angle of 180°, the radial protrusions 21, 22 pull the engagement means 12 towards the main body 14 and, thereby, cause a refraction of the engagement means 12. This orientation of the switching member is shown in FIGS. 4A and 4B and may be denoted as "6 o'clock orientation".

In the following, the working principle of the switching member 18 is described in more detail.

Each thread form 16 of the engagement means 12 is located on a ring-shaped member 24, which is movable back and forth in a radial direction 25 relative to the main body 14. When the switching member 18 is rotated around the longitudinal axis 5 in a rotational direction 26 by an angle of 180°, the protrusions 21, 22 urge the ring-shaped members 24 and, thereby, the engagement means 12 in the radial direction 25, such that the engagement means 12 are retracted towards the main body 14.

FIG. 4A shows a perspective sectional view of the first embodiment of the piston rod 9 in its reset state. FIG. 4B shows a perspective cross-sectional view of the piston rod of FIG. 4A.

The switching member 18 has been rotated to its 6 o'clock position, such that the thread forms 16 are retracted towards the main body 14. The engagement means 12 may be fully retracted into the main body 14 such that they do not protrude to the outside, may be flush with an outer surface of the main body 14 or may be only partially retracted towards the main body 14 such that they protrude from the main body 14 to a minor extent. In all cases, the engagement means 12 are retracted such that a disengagement from a part of the drug delivery device 1, for example the nut member 13 as shown in FIG. 2 is enabled. In this state of the piston rod 9, a reset movement of the piston rod 9 is facilitated.

In the following, a possible reset operation of a drug delivery device comprising the switching member as shown in FIGS. 3A to FIG. 4B is described in detail.

When a cartridge holder 3 of a drug delivery device 1, for example as shown in FIG. 1, is detached from a main housing 2 to exchange a cartridge, the switching member 18 may be operated such that the engagement means 12 are retracted towards the main body 14 of the piston rod 9, thereby switching the piston rod 9 from an operational state into a reset state.

An operation of the switching member 18 may be accomplished in different ways according to the specific design of the piston rod 9 or a respective drug delivery device 1. As an example, the switching member 18 may be coupled to a dose member 8 such that a rotation of the dose member 8 causes a rotation of the switching member 18. In particular, the proximal end of the switching member 18 which extends in axial direction from the main housing 14 as shown in FIG. 3A, for example, may be coupled to the dose member 8. In a further embodiment, the switching member 18 may be coupled to a cartridge holder 3 of the device 1 such that a detachment operation of the cartridge holder 3 causes a rotation of the switching member 18. In particular, the piston rod 9 may be switched to its reset state automatically when the cartridge holder 4 is detached.

When switched to its reset state, the piston rod 9 may be moved back towards a proximal start position. As the piston rod 9 is disengaged from a part of the drug delivery device, the movement is unhindered by the part of the drug delivery device. Depending on the design of the device, the piston rod may be pushed back in the proximal direction or may be wound back in the proximal direction.

When the piston rod 9 is in a proximal start position, it may be switched from its reset state to its operational state such that the engagement means 12 reengage with the part of the drug delivery device. Also here, the switching operation may be caused by a rotation of the dose member 8 or automatically by an attachment operation of the cartridge holder 4, as example.

Figure 5:
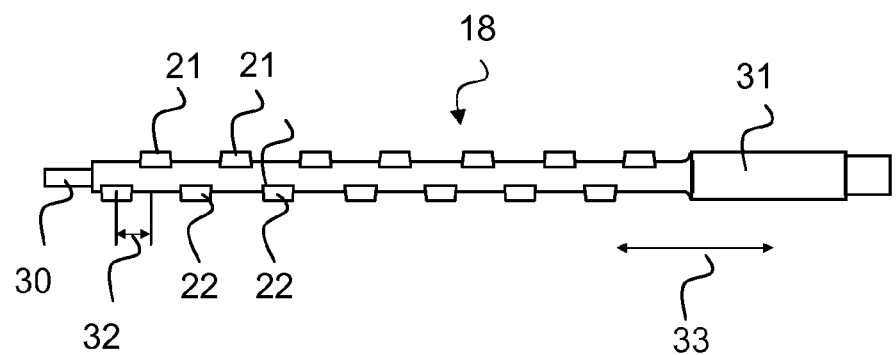
FIG. 5 shows a side view of a switching member.

FIG. 5 shows a side view of a switching member 18, which may be used in a second embodiment of a piston rod 9.

Figure 6:
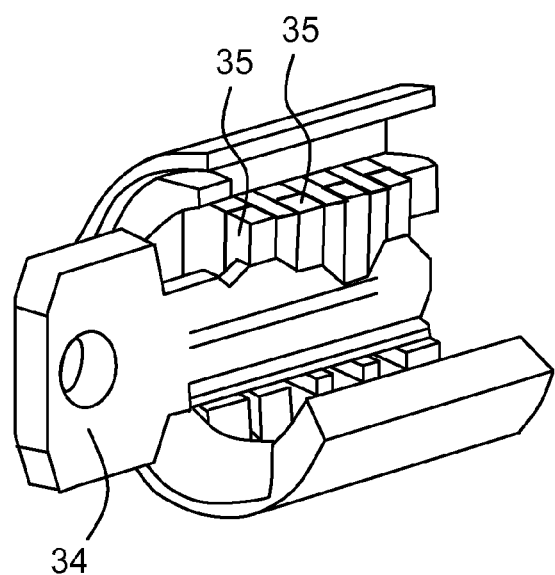
FIG. 6 shows a schematic perspective cut-away view of a working principle of a second embodiment of a piston rod.

According to the second embodiment, engagement means 12 of the piston rod 9 are extended and retracted by a sliding movement of the switching member 18. Accordingly, the switching member 18 may function as a sliding camshaft. The sliding cam operation may be similar to a key in a lock barrel as shown in FIG. 6. The key 34 corresponds to the switching member 18 of the piston rod 9. Lock members 35 correspond to protrusions 21, 22 of the switching member 18.

The switching member 18 comprises a number of protrusions 21, 22 extending in opposite radial directions. The respective piston rod 9 is configured such that when the switching member 18 is moved axially by half the length of the pitch 32 of the protrusions 21, 22 in an axial direction 33, the engagement means 12 of the piston rod 9 extend out of the main body 14 of the piston rod 9. When the switching member 18 is moved in the opposite direction, the engagement means 12 are urged back to the main body 14. The design of the engagement means 12 and the main body 14 of the piston rod 9 may be identical or similar to the design as shown in FIGS. 3A to 4B.

The invention claimed is:

1. A piston rod for a drug delivery device, the piston rod comprising:
    a main body comprising a longitudinal axis and engagement means for engaging the piston rod with a part of the drug delivery device, wherein the engagement means are radially retractable relative to the longitudinal axis of the main body for enabling a disengagement of the engagement means from the part of the drug delivery device, wherein the main body comprises a plurality of openings in an outer surface of the main body, and wherein the engagement means comprise a plurality of threaded forms which are retractable through the plurality of openings.

2. The piston rod of claim 1, comprising a switching member configured such that an operation of the switching member causes at least one of an extension or retraction of the engagement means relative to the main body.

3. The piston rod of claim 2, configured such that an operation of the switching member comprises a rotational movement of the switching member.

4. The piston rod of claim 2, configured such that an operation of the switching member comprises a translational movement of the switching member.

5. The piston rod of claim 2, wherein the switching member is at least partially located inside the main body of the piston rod.

6. The piston rod of claim 2, wherein the switching member comprises at least one protrusion and wherein the piston rod is configured such that the engagement means is at least one of extended and retracted by an interaction of the engagement means with the protrusion.

7. The piston rod of claim 2, wherein the switching member comprises a cam shaft.

8. A drug delivery device comprising a piston rod of claim 1.

9. The drug delivery device of claim 8, comprising a main housing and a cartridge holder attachable to and detachable from the main housing.

10. The drug delivery device of claim 9, configured such that the piston rod is resettable to a start position when the cartridge holder is detached from the main housing.

11. The drug delivery device of claim 8, comprising a dose member for setting and/or dispensing a dose of a medication, wherein an operation of the dose member causes at least one of a retraction or extension of the engagement means.

12. The drug delivery device of claim 9, configured such that a detachment of the cartridge hold causes a retraction of the engagement means.

* * * * *